United States Patent [19]

Minai et al.

[11] Patent Number: 4,511,655
[45] Date of Patent: Apr. 16, 1985

[54] PROCESS FOR PRODUCING 4-CYCLOPENTENONES

[75] Inventors: Masayoshi Minai, Moriyama; Tadashi Katsura, Osaka, both of Japan

[73] Assignee: Sumitomo Chemical Company, Limited, Osaka, Japan

[21] Appl. No.: 443,017

[22] Filed: Nov. 19, 1982

[30] Foreign Application Priority Data

Nov. 19, 1981 [JP] Japan ............................... 56-186658
Dec. 25, 1981 [JP] Japan ............................... 56-212393
Mar. 15, 1982 [JP] Japan ............................... 57-41207

[51] Int. Cl.³ .......................... C12P 7/38; C12P 7/62; C07B 19/02
[52] U.S. Cl. ................................... 435/149; 435/135; 435/280
[58] Field of Search ................... 435/280, 149, 135

[56] References Cited

U.S. PATENT DOCUMENTS

| | | | |
|---|---|---|---|
| 3,432,393 | 3/1969 | Bellet et al. | 435/149 |
| 3,607,651 | 9/1971 | Moroe et al. | 435/280 |
| 3,907,638 | 9/1975 | Uzuki et al. | 435/280 |
| 4,022,664 | 5/1977 | Kawamura et al. | 435/280 |

OTHER PUBLICATIONS

Oritani et al., "Microbial Resolution of Some Racemic Monocyclic Alcohols", Agr. Biol. Chem., 39(1), 89–96, (1975).

Primary Examiner—Alvin E. Tanenholtz
Attorney, Agent, or Firm—Birch, Stewart, Kolasch & Birch

[57] ABSTRACT

A 4-cyclopentenone of the formula:

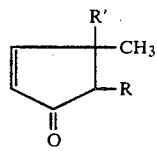

wherein R is a lower alkyl group, a lower alkenyl group or a lower alkynyl group and R' is a hydroxyl group or an aliphatic acyloxy group, provided that in case of the dl-form, R' is not a hydroxyl group and also that the substituent R at the 2-position and the methyl group at the 3-position take a cis-configuration in the dl-, d- or l-form.

11 Claims, No Drawings

PROCESS FOR PRODUCING 4-CYCLOPENTENONES

The present invention relates to 4-cyclopentenones and their production. More particularly, it relates to 4-cyclopentenones of the formula:

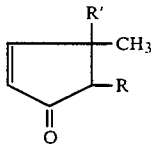
(I)

wherein R is a lower alkyl group, a lower alkenyl group or a lower alkynyl group and R' is a hydroxyl group or an aliphatic acyloxy group such as lower alkanoyl, provided that in case of the dl-form, R' is not a hydroxyl group and also that the substituent R at the 2-position and the methyl group at the 3-position take a cis-configuration, and their production.

The 4-cyclopentenones (I) cover not only the dl-form but also the d-form and the l-form. Further, the term "lower" as used hereinabove is intended to mean not more than 8 carbon atoms.

The 4-cyclopentenones (I) are novel. They are per se useful as agricultural chemicals and also as intermediates in the synthesis of agriculatural chemicals, pharmaceuticals (e.g. prostaglandins), perfumes, etc. For instance, rearrangement of l-2-allyl-3-hydroxy-3-methyl-4-cyclopentenone (I: R=—CH$_2$CH=CH$_2$; R'=—OH) while keeping its steric configuration gives S(+)-4-hydroxy-2-allyl-3-methyl-2-cyclopentenone (i.e. allethrolone) predominantly. This product is an important agricultural chemical. Likewise, rearrangement of d-2-substituted-3-hydroxy-3-methyl-4-cyclopentenones (I: R=optional substituent, i.e. lower alkyl, lower alkenyl or lower alkynyl; R'=—OH) affords R(—)-2-substituted-4-hydroxy-3-methyl-2-cyclopentenones selectively, which may be utilized as intermediates in the synthesis of prostaglandins. According to this invention, the 4-cyclopentenones (I) in the d-, l- or dl-form can be provided cheaply and conveniently.

The 4-cyclopentenones (I) cover dl-2-substituted-3-acyloxy-3-methyl-4-cyclopentenones (Ia), d- or l-2-substituted-3-hydroxy-3-methyl-4-cyclopentenones (Ib) and d- or l-2-substituted-3-acyloxy-3-methyl-4-cyclopentenones (Ic).

Among the objective 4-cyclopentenones (I), dl-2-substituted-3-acyloxy-3-methyl-4-cyclopentenones (Ia) can be produced easily in a good yield by reacting dl-3-hydroxy-4-cyclopentenones of the formula:

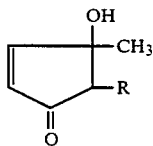
(II)

wherein R is as defined above and the substituent R at the 2-position and the methyl group at the 3-position take a cis-configuration with an aliphatic carboxylic acid halide or anhydride in the presence or absence of any appropriate solvent.

The starting dl-3-hydroxy-4-cyclopentenones (II) may be prepared, for instance, by rearrangement of the corresponding carbinols as shown in the following formulas (Japanese Patent Publication (unexamined) No. 38741/82):

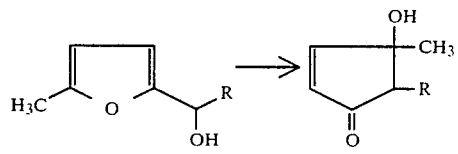

wherein R is as defined above. Specific examples of the 3-hydroxy-4-cyclopentenones (II) are as follows: 3-hydroxy-2,3-dimethyl-4-cyclopentenone, 2-ethyl-3-hydroxy-3-methyl-4-cyclopentenone, 3-hydroxy-2-n-propyl-3-methyl-4-cyclopentenone, 2-isopropyl-3-hydroxy-3-methyl-4-cyclopentenone, 3-hydroxy-2-n-butyl-3-methyl-4-cyclopentenone, 2-isobutyl-3-hydroxy-3-methyl-4-cyclopentenone, 3-hydroxy-2-n-pentyl-3-methyl-4-cyclopentenone, 2-isopentyl-3-hydroxy-3-methyl-4-cyclopentenone, 3-hydroxy-2-n-hexyl-3-methyl-4-cyclopentenone, 3-hydroxy-2-n-heptyl-3-methyl-4-cyclopentenone, 2-allyl-3-hydroxy-3-methyl-4-cyclopentenone, 3-hydroxy-2-ω-butenyl-3-methyl-4-cyclopentenone, 3-hydroxy-(2-cis-butenyl)-3-methyl-4-cyclopentenone, 3-hydroxy-2-(2-cis-pentenyl)-3-methyl-4-cyclopentenone, 3-hydroxy-2-(2-trans-pentenyl)-3-methyl-4-cyclopentenone, 3-hydroxy-2-(3-cis-hexenyl)-3-methyl-4-cyclopentenone, 3-hydroxy-3methyl-2-(α-methylallyl-4-cyclopentenone, 3-hydroxy-2-propargyl-3-methyl-4-cyclopentenone, 3-hydroxy-2-(2-pentynyl)-3-methyl-4-cyclopentenone, etc.

As the aliphatic carboxylic acid halide or anhydride as the other starting material, there may be exemplified lower alkanoic acid halides and anhydrides, lower alkenoic acid halides and anhydrides, halo(lower)alkanoic acids and their halides and anhydrides, etc. Specific examples are, acetyl chloride, acetyl bromide, acetic anhydride, propionyl chloride, propionyl bromide, butyryl chloride, butyryl bromide, caproyl chloride, caproyl bromide, capryloyl chloride, capryloyl bromide, caprinoyl chloride, caprinoyl bromide, dodecanoyl chloride, dodecanoyl bromide, palmitoyl chloride, palmitoyl bromide, chloroacetyl chloride, chloracetyl bromide, dichloroacetyl chloride, dichloroacetyl bromide, etc.

The reaction may be carried out under the conditions as conventionally adopted for esterification, for instance, in the presence or absence of an inert solvent in the existence of a catalyst. Examples of the inert solvent are aliphatic or aromatic hydrocarbons, halogenated hydrocarbons, ethers, etc. Specific examples are tetrahydrofuran, ethyl ether, acetone, methyl ethyl ketone, toluene, benzene, chlorobenzene, dichloromethane, dichloroethane, chloroform, carbon tetrachloride, dimethylformamide, hexane, etc. As the catalyst, there may be exemplified organic bases such as triethylamine, tri-n-butylamine, pyridine and picoline and inorganic bases such as sodium carbonate, sodium methoxide and potassium hydrogen carbonate. When an organic amine is used as the solvent, it can simultaneously serve as the catalyst. Further, a dehydrating agent such as toluenesulfonic acid, methanesulfonic acid or sulfuric acid may be used as the catalyst.

In the reaction, the aliphatic carboxylic acid halide or anhydride may be used in an amount of not less than one equivalent, preferably of from 1 to 4 equivalents, to the dl-3-hydroxy-4-cyclopentenone (II). The amount of the catalyst may be usually from 1 to 5 equivalents to the dl-3-hydroxy-4-cyclopentenone (II).

The reaction temperature is usually from −20° to 150° C., preferably from −10° to 120° C. There is no limit on the reaction time.

Recovery of the produced dl-2-substituted-3-acyloxy-3-methyl-4-cyclopentenone (Ia) from the reaction mixture may be accomplished by a per se conventional separation procedure such as extraction, fractionation, concentration and distillation.

Further, the optically active forms of the 4-cyclopentenones (I), i.e. d- or l-2-substituted-3-hydroxy-3-methyl-4-cyclopentenones (Ib) and d- or l-2-substituted-3-acyloxy-3-methyl-4-cyclopentenones (Ic), can be produced by subjecting the dl-2-substituted-3-acyloxy-3-methyl-4-cyclopentenones (Ia) to asymmetric hydrolysis with a microorganism or an enzyme.

As the microorganism, there may be used any one which can hydrolyze only the d- or l-form in the dl-2-substituted-3-acyloxy-3-methyl-4-cyclopentenones (Ia) at the acyloxy group. Those microorganisms may be chosen from Rhodotorula, Trichoderma, Candida, Pseudomonas, Hansenula, Bacillus, Achromobacter, Nocardia, Chromobacterium, Flavobacterium, Rhizopus, Mucor, Aspergillus, Alcaligenes, Torulopsis, Corynebacterium, Endomyces, Saccharomyces, Arthrobacter, Metshnikowia, Pleurotus, Streptomyces, Proteus, Gliocladium, Acetobacter, Helminthosporium, Brevibacterium, Escherichia, Citrobacter, Micrococcus, Pediococcus, Klebsiella, Absidia, Geotrichem, etc. as well as from lichen, algae, etc. Specific examples are *Rhodotorula minuta* (IFO-0387, IFO-0412), *Rhodotorula rubra* (IFO-0870), *Rhodotolura minuta* var. *texensis* (IFO-0879), *Trichoderma longibrachiatum* (IFO-4847), *Candida krusei* (OUT-6007), *Candida cylindracea, Candida tropicalis* (PK 233), *Candida utilus* (IFO-1086), *Pseudomonas fragi* (IFO-3458), *Pseudomonas putida* (IFO-12996), *Pseudomonas fluorescens* (IFO-3903), *Pseudomonas aeruginosa* (IFO-3080), *Hansenula anomala* var. *ciferrii* (OUT-6095), Hansenula anomala (IFO-0118), *Hansenula polymorpha* (IFO-1475), *Bacillus cereus* (IFO-3466), *Bacillus subtilis* (ATCC-6633), *Bacillus pumilus* (IFO-12092), *Bacillus subtilis* var. *niger* (IFO-3108), *Achromobacter lyticus* (ATCC-21456), *Achromobacter parvulus* (IFO-13181), *Achromobacter simplex* (IFO-12069), *Nocardia uniformis subptsuyamanenus* (ATCC-21806), *Nocardia uniformis* (IFO-13072), *Chromobacterium chocolatum* (IFO-3758), *Chromobacterium iodinum* (IFO-3558), *Chromobacter violaceum* (IFO-12614), *Flavobacterium lutescens* (IFO-3084), *Flavobacterium arbonescens* (IFO-3750), *Flavobacterium heparinum* ((IFO-12017), *Flavobacterium capsulatum* (IFO-12533), *Rhizopus chinensis* (IFO-4768), *Mucor pusillus* (IFO-9856), *Aspergillus niger* (ATCC-9642), *Alkaligenes faecalis* (IFO-12669), *Torulopsis ernobii* (IFO-0654), *Torulopsis candida* (IFO-0768), *Corynebacterium sepedonicum* (IFO-13763), *Endomyces geotrichum* (IFO-9542), *Saccharomyces cerevisiae* (IFO-0334), *Arthrobacter globiformis* (IFO-12137), *Metschnikowia pulcherrima* (IFO-0561), *Pleurotus ostreatus* (IFO-7051), *Streptomyces griseus* (IFO-3356), *Proteus vulgaris* (IFO-3851), *Proteus unigavic* (IID-874), *Gliocladium roseum* (IFO-5422), *Gliocladium virens* (IFO-6355), *Acetobacter aurantius* (IFO-3247), *Helminthosporium* sp. (ATTC-20154), *Brevibacterium ammoniagenes* (IFO-12072), *Brevibacterium dinaricatum* (ATCC-14020), *Escherichia coli* (IFO-12713, IFO-3302, IFO-13168), *Citrobacter freundii* (IFO-12681), *Micrococcus varianaes* (IFO-3765), *Micrococcus lutens* (IFO-3066), *Pediococcus acidilacticie* (IFO-3076), *Klebsiella pneumorial* (IFO-12059), *Absidia hyalospora* (IFO-8082), *Geotrichum candidum* (IFO-4597), etc.

As the enzyme, there may be used anyone having a capability of hydrolyzing only one of the d- or l-form in the dl-2-substituted-3-acyloxy-3-methyl-4-cyclopentenones (I) at the acyloxy group, which may be obtained from animals, plants, microorganisms, etc. The enzyme may be employed in any conventional form such as a purified form, a crude form, a mixture with other enzymes, a fermentation broth, a microbial body, a filtrate of fermentation broth, etc. Specific examples of the enzyme are those obtainable from animals and plants such as pig liver esterase, pig pancreas esterase, horse liver esterase, dog liver esterase, pig phosphatase, β-amylase obtainable from barley and potato and lipase obtainable from wheat. Other examples are hydrolases obtainable from microorganisms as hereinabove mentioned.

The microorganism and the enzyme may be used alone or in combination. Depending upon the kind of the microorganism or the enzyme as used, l-2-substituted-3-acyloxy-3-methyl-4-cyclopentenone or d-2-substituted-3-acyloxy-3-methyl-4-cyclopentenone is predominantly hydrolyzed to give d-2-substituted-3-hydroxy-3-methyl-4-cyclopentenone or l-2-substituted-3-hydroxy-3-methyl-4-cyclopentenone. Thus, it is a great characteristic of this invention that either of the d-form or the l-form can be optionally produced by selection of a suitable microorganism or enzyme.

Since asymmetric reduction is hardly applicable to tertiary alcohols, it may be said that the production of the optically active forms of the 4-cyclopentenones (I) are extremely difficult. Quite surprisingly, the hydrolytic process of this invention can accomplish the hydrolysis of tertiary alcohol esters such as the dl-2-substituted-3-acyloxy-3-methyl-4-cyclopentenones (Ia) with a good optical purity. Further, either of the d-form and the l-form is optionally obtainable by application of such hydrolytic process.

For selective hydrolysis of d-2-substituted-3-acyloxy-3-methyl-4-cyclopentenones to l-2-substituted-3-hydroxy-3-methyl-4-cyclopentenones, the following microorganisms or enzymes are preferably employed: pig liver esterase, horse liver esterase, *Candida cyclindracea, Hansenula anomala* var. *ciferrii* (OUT-6095), *Metshnikowia pulcherrima* (IFO-0561), *Pleurotus ostreatus* (IFO-7051), cholesterol esterase (from *Schizophyllum commune*), *Candida krusei* (OUT-6007), etc. For selective hydrolysis of l-2-substituted-3-acyloxy-3-methyl-4-cyclopentenones to d-2-substituted-3-hydroxy-3-methyl-4-cyclopentenones, the use of the following microorganisms or enzymes is preferred: *Pseudomonas fragi* (IFO-3458), *Pseudomonas fluorescens* (IFO-3903), Pseudomonas aeruginosa (IFO-3080), etc. and enzymes produced by those microorganisms.

As understood from the above, not only dl-2-substituted-3-acyloxy-3-methyl-4-cyclopentenones but also 2-substituted-3-acyloxy-3-methyl-4-cyclopentenones containing the d- or l-isomer in an excessive amount separated from the reaction mixture after the hydrolysis are usable as the starting material for hydrolysis.

The hydrolysis may be carried out by contacting the dl-4-cyclopentenones (I), which may contain optionally either one of the d- and l-isomers in an excessive amount, with the said microorganism or enzyme, usually in a buffer medium while stirring vigorously. As the buffer medium, there are usually employed inorganic salt buffers (e.g. sodium phosphate, potassium phosphate), organic salt buffers (e.g. sodium citrate), etc. These buffers have usually a pH of 4 to 10, preferably 5 to 9. The concentration of the buffer may be usually from 0.05 to 2M, preferably from 0.05 to 0.5M. The reaction temperature may be normally from 20° to 40° C., and the reaction time is generally from 10 to 70 hours.

In order to achieve a better optical yield in the hydrolysis, it is preferred to interrupt the hydrolysis at an appropriate stage depending upon the optical composition of the starting material. When, for instance, the dl-4-cyclopentenones (I) are used, the hydrolysis is favorably finished with a reaction rate of less than 50%.

In case of using a microorganism belonging to Pseudomonas or an enzyme produced thereby, only the l-isomers in the dl-4-cyclopentenones (I) are hydrolyzed to d-2-substituted-3-hydroxy-3-methyl-4-cyclopentenones (I: R'=—OH) leaving the d-isomers in the dl-4-cyclopentenones as such, i.e. d-2-substituted-3-acyloxy-3-methyl-4-cyclopentenones.

In case of using a microorganism belonging to Candida or an enzyme produced thereby, only the d-isomers in the dl-4-cyclopentenones are hydrolyzed to l-2-substituted-3-hydroxy-3-methyl-4-cyclopentenones (I: R'=—OH) leaving the l-isomers in the dl-4-cyclopentenones as such, i.e. l-2-substituted-3-acyloxy-3-methyl-4-cyclopentenones.

For recovery of the optical isomers from the reaction mixture, they may be extracted with an appropriate solvent (e.g. methyl isobutyl ketone, ethyl acetate, ethyl ether). The extract is concentrated, and the residue is purified, for instance, by column chromatography to isolate d- or l-2-substituted-3-hydroxy-3-methyl-4-cyclopentenones and d- or l-2-substituted-3-acyloxy-3-methyl-4-cyclopentenones.

Examples of the 4-cyclopentenones (I) obtainable by the present invention are as follows: d- or l-isomers of 3-hydroxy-2,3-dimethyl-4-cyclopentenone, 2-ethyl-3-hydroxy-3-methyl-4-cyclopentenone, 3-hydroxy-2-n-propyl-3-methyl-4-cyclopentenone, 2-isopropyl-3-hydroxy-3-methyl-4-cyclopentenone, 3-hydroxy-2-n-butyl-3-methyl-4-cyclopentenone, 2-isobutyl-3-hydroxy-3-methyl-4-cyclopentenone, 3-hydroxy-2-n-pentyl-3-methyl-4-cyclopentenone, 2-isopentyl-3-hydroxy-3-methyl-4-cyclopentenone, 3-hydroxy-2-n-hexyl-3-methyl-4-cyclopentenone, 3-hydroxy-2-n-heptyl-3-methyl-4-cyclopentenone, 2-allyl-3-hydroxy-3-methyl-4-cyclopentenone, 3-hydroxy-2-ω-butenyl-3-methyl-4-cyclopentenone, 3-hydroxy(2-cis-butenyl)-3-methyl-4-cyclopentenone, 3-hydroxy-2-(2-cis-pentenyl)-3-hydroxy-3-methyl-4-cyclopentenone, 3-hydroxy-2-(2-trans-pentenyl)-3-methyl-4-cyclopentenone, 3-hydroxy-2-(3-cis-hexenyl)-3-methyl-4-cyclopentenone, 3-hydroxy-3-methyl-2-(α-methylallyl)-4-cyclopentenone, 3-hydroxy-2-propargyl-3-methyl-4-cyclopentenone, 3-hydroxy-2-(2-pentynyl)-3-methyl-4-cyclopentenone, etc.; d- or l-isomers of 3-acetoxy-2,3-dimethyl-4-cyclopentenone, 3-acetoxy-2-ethyl-3-methyl-4-cyclopentenone, 3-acetoxy-2-n-propyl-3-methyl-4-cyclopentenone, 3-acetoxy-2-isopropyl-3-methyl-4-cyclopentenone, 3-acetoxy-2-n-butyl-3-methyl-4-cyclopentenone, 3-acetoxy-2-isobutyl-3-methyl-4-cyclopentenone, 3-acetoxy-2-n-pentyl-3-methyl-4-cyclopentenone, 3-acetoxy-2-isopentyl-3-methyl-4-cyclopentenone, 3-acetoxy-2-n-hexyl-3-methyl-4-cyclopentenone, 3-acetoxy-2-n-heptyl-3-methyl-4-cyclopentenone, 3-acetoxy-2-allyl-3-methyl-4-cyclopentenone, 3-acetoxy-2-ω-butenyl-3-methyl-4-cyclopentenone, 3-acetoxy-(2-cis-butenyl)-3-methyl-4-cyclopentenone, 3-acetoxy-2-(2-cis-pentenyl)-3-hydroxy-3-methyl-4-cyclopentenone, 3-acetoxy-2-(2-trans-pentenyl)-3-methyl-4-cyclopentenone, 3-acetoxy-2-(3-cis-hexenyl)-3-methyl-4-cyclopentenone, 3-acetoxy-3-methyl-2-(α-methylallyl)-4-cyclopentenone, 3-acetoxy-2-propargyl-3-methyl-4-cyclopentenone, 3-acetoxy-2-(2-pentynyl)-3-methyl-4-cyclopentenone, etc.; d- or l-isomers of the propionyloxy compounds corresponding to the acetoxy compounds as exemplified above; d- or l-isomers of the octanoyloxy compounds corresponding to the acetoxy compounds as exemplified above.

Practical and presently preferred embodiments of the invention are illustratively shown in the following Examples wherein part(s) and % are by weight unless otherwise indicated.

EXAMPLE 1

Into a flask equipped with a stirrer and a thermometer, dl-2-allyl-3-hydroxy-3-methyl-4-cyclopentenone (30.4 g), pyridine (30 g) and dichloromethane (300 g) were charged, and acetyl chloride (30 g) was dropwise added thereto at a temperature from 10° to 20° C. in 2 hours. Then, stirring was continued at a room temperature for 24 hours. To the reaction mixture kept below 10° C., water (100 ml) was added to decompose excess of acetyl chloride. From the resultant mixture, the organic layer was separated and washed with 1% hydrochloric acid, 1% sodium bicarbonate solution and water in order. Removal of the solvent by distillation gave dl-3-acetoxy-2-allyl-3-methyl-4-cyclopentenone (36.5 g). Yield, 94%.

$n_D^{25}$ 1.4803. B.P., 72°–74° C./0.2 mmHg.

Elementary analysis: Calcd.: C, 68.02%; H, 7.26%. Found: C, 68.11%; H, 7.30%.

EXAMPLE 2

Into the same flask as in Example 1, dl-2-allyl-3-hydroxy-3-methyl-4-cyclopentenone (15.2 g), pyridine (15 g) and dichloromethane (150 g) were charged, and chloroacetyl chloride (22.5 g) was dropwise added thereto at a temperature from 10° to 15° C. in 3 hours. Then, stirring was continued at room temperature for 24 hours. To the reaction mixture kept below 10° C., water (50 ml) was added to decompose excess of acetyl chloride. The resulting mixture was treated as in Example 1. The residue was purified by silica gel chromatography using a mixture of toluene and ethyl acetate (10:1) as an eluent to give dl-2-allyl-3-chloroacetyloxy-3-methyl-4-cyclopentenone (20.7 g). Yield, 91%.

$n_D^{20}$ 1.4865.

Elementary analysis: Calcd.: C, 57.55%; H, 5.73%; Cl, 15.50%. Found: C, 57.86%; H, 5.88%; Cl, 14.95%.

EXAMPLE 3

Into the same flask as in Example 1, 3-hydroxy-2-n-pentyl-3-methyl-4-cyclopentenone (18.2 g), triethylamine (20.3 g) and chloroform (150 g) were charged, and acetyl chloride (15.8 g) was dropwise added thereto at a temperature of 10° to 15° C. in 2 hours. Then, stirring was continued at room temperature for 20 hours. The reaction mixture was treated as in Example 1. The residue was purified by silica gel chromatography using a mixture of toluene and ethyl acetate (10:1) as an eluent to give dl-3-acetoxy-2-n-pentyl-3-methyl-4-cyclopentenone (21.5 g). Yield, 96%.

$n_D^{20}$ 1.4696.

Elementary analysis: Calcd.: C, 69.61%; H, 8.98%. Found: C, 69.77%; H, 8.81%.

EXAMPLES 4 TO 10

In the same manner as in Example 1, there were produced various 4-cyclopentenones (I). The results are shown in Table 1.

rotation, $[\alpha]_D^{20}$ −91.8° (C=1, chloroform); $n_D^{20}$ 1.4801).

REFERENCE EXAMPLE 1

The above obtained 1-2-allyl-3-hydroxy-3-methyl-4-cyclopentenone (0.5 g), alumina (10 g) and benzene (30 ml) were mixed together while stirring at 50°–60° C. for 6 hours. The alumina was collected by filtration and washed with methanol (10 ml) two times. The filtrate was concentrated and the residue was purified by col-

TABLE 1

| Example No. | Starting materials | | Aliphatic carboxylic acid derivative | Catalyst (part(s)) | Solvent (part(s)) | Reaction condition | | | | 4-Cyclopentenone (I) (dl-form) | | |
|---|---|---|---|---|---|---|---|---|---|---|---|---|
| | 3-Hydroxy-4-cyclopentenone (II) | | | | | Dropping | | Retaining | | | Yield (%) | Physical constant |
| | R | R' | | | | Temp. (°C.) | Time (hr) | Temp. (°C.) | Time (hr) | R' | | |
| 4 | CH₂CH=CH₂ | OH | Caprylol chloride (2.5) | Pyridine (3) | Dichloromethane (5) | 10–20 | 3 | Room temp. | 25 | n-C₇H₅COO— | 92 | $n_D^{20}$ 1.4757 |
| 5 | CH₂CH=CH₂ | OH | n-Decanoyl chloride (2.5) | Triethylamine (2.5) | Tetrahydrofuran (5) | 10–20 | 2 | Room temp. | 25 | n-C₁₉H₁₉COO— | 91 | $n_D^{20}$ 1.4751 |
| 6 | CH₃ | OH | Acetyl chloride (1.5) | Pyridine (2) | Chloroform (5) | 15–25 | 2 | Room temp. | 20 | CH₃COO— | 95 | $n_D^{20}$ 1.4721 |
| 7 | n-C₅H₁₁ | OH | Capryloyl chloride chloride (2) | Pyridine (2) | Dichloromethane (5) | 10–20 | 2 | Room temp. | 30 | n-C₇H₁₅COO— | 93 | $n_D^{20}$ 1.4735 |
| 8 | CH₂CH=CHC₂H₅ (cis) | OH | Acetyl chloride (1.5) | Pyridine (2) | Dichloromethane (5) | 10–20 | 2 | Room temp. | 25 | CH₃COO— | 96 | $n_D^{20}$ 1.4817 |
| 9 | CH₂C≡CH | OH | Acetyl chloride (1.5) | Pyridine (2) | Dichloromethane (5) | 10–20 | 2 | Room temp. | 25 | CH₃COO— | 95.5 | $n_D^{20}$ 1.4912 |
| 10 | CH₂CH=CH₂ | OH | Crotonyl chloride (2) | Pyridine (3) | Dichloromethane (5) | 10–20 | 2 | Room temp. | 20 | CH₃CH=CHCOO— | 92 | $n_D^{20}$ 1.4865 |

EXAMPLE 11

Into the same flask as used in Example 1, 2-allyl-3-hydroxy-3-methyl-4-cyclopentenone (152 g), p-toluenesulfonic acid (1 g) and acetic anhydride (320 g) were charged, and stirring was continued for 2 hours at 100° C. After completion of the reaction, acetic anhydride was removed under reduced pressure, and the residue was extracted with toluene. The toluene layer was washed with 1% aqueous sodium carbonate solution and water in order and concentrated to give dl-3-acetoxy-2-allyl-3-methyl-4-cyclopentenone (186 g). Yield, 96%. B.P., 72°–75° C./0.2–0.3 mmHg.

The thus obtained dl-3-acetoxy-2-allyl-3-methyl-4-cyclopentenone (5 g), Porcine Liver Esterase (manufactured by Sigma Inc.) (300 mg) and 0.1M phosphate buffer (200 ml; pH 7.0) were mixed together, and the resultant mixture was stirred at 25°–30° C. for 24 hours. After completion of the reaction, the reaction mixture was extracted with methylisobutylketone (50 ml) three times. The solvent was removed from the extract, and the residue was purified by column chromatography using a mixture of ethyl acetate and toluene (3:5) as an eluent to give 1.84 g of 1-2-allyl-3-hydroxy-3-methyl-4-cyclopentonene (yield, 47%; optical rotation, $[\alpha]_D^{20}$ −23.9° (C=1, chloroform); $n_D$ 1.4983) and 2.5 g of 1-acetoxy-2-allyl-3-methyl-4-cyclopentenone (optical umn chromatography using a mixture of toluene and ethyl acetate (5:2) as an eluent to give 0.43 g of S(+)-2-allyl-4-hydroxy-3-methyl-2-cyclopentenone. Optical purity, 98% (determined by the method as described in Agr.Biol.Chem., 41 (10), 2003–2006 (1977)).

EXAMPLE 12

Into the same flask as used in Example 1, 3-hydroxy-2-propargyl-3-methyl-4-cyclopentenone (30 g) and acetic anhydride (70 g) were charged, and the resultant mixture was stirred at 100° to 120° C. for 3 hours. After completion of the reaction, the reaction mixture was subjected to the same work-up as in Example 11, followed by purification to give 36.4 g of dl-3-acetoxy-2-propargyl-3-methyl-4-cyclopentenone. Yield, 95%. B.P., 82°–86° C./0.2–0.3 mmHg.

The thus obtained dl-3-acetoxy-2-propargyl-3-methyl-4-cyclopentenone (2 g), Porcine Liver Esterase (manufactured by Sigma Inc.) (80 mg) and 0.1M phosphate buffer (80 ml; pH 6) were mixed together, and the resultant mixture was vigorously stirred at 35° C. for 20 hours. After completion of the reaction, the reaction mixture was extracted with methylisobutylketone (40 ml) three times. The solvent was removed from the extract, and the residue was purified by column chromatography using a mixture of ethyl acetate and toluene (3:5) as an eluent to give 0.72 g of 1-3-hydroxy-3-methyl-2-propargyl-4-cyclopentenone (yield, 46.1%; optical rotation, $[\alpha]_D^{20}$ −131.7° (C=1, chloroform); M.P., 61° C.) and 0.96 g of l-3-acetoxy-2-propargyl-3-methyl-4-cyclopentenone (optical rotation, $[\alpha]_D^{20}$ −16.2° (C=1, chloroform); $n_D^{20}$ 1.4943)).

The optical purity of d-4-hydroxy-2-propargyl-3-methyl-2-cyclopentenone obtained by rearrangement of l-3-hydroxy-2-propargyl-3-methyl-4-cyclopentenone according to Reference Example 1 was 97.5%.

EXAMPLE 13

Into the same flask as used in Example 1, dl-3-hydroxy-2-(ω-butenyl)-3-methyl-4-cyclopentenone (16.6 g) and acetic anhydride (35 g) were charged, and the resultant mixture was stirred at 100°–120° C. for 3 hours. After completion of the reaction, the reaction mixture was subjected to the same work-up as in Example 11, followed by purification to give 19.6 g of dl-3-acetoxy-2-(ω-butenyl)-3-methyl-4-cyclopentenone. Yield, 96%. B.P., 81°–85° C./0.2 mmHg.

The thus obtained dl-3-acetoxy-2-ω-butenyl-3-methyl-4-cyclopentenone (2 g), Porcine Liver Esterase (manufactured by Sigma Inc.) (80 mg) and 0.1M phosphate buffer (100 ml; pH 8.0) were mixed together, and the resultant mixture was vigorously stirred at 25°–30° C. for 24 hours. After completion of the reaction, the reaction mixture was extracted with methylisobutylketone (40 ml) three times. The same work-up as in Reference Example 1 gave 0.68 g of l-3-hydroxy-2-ω-butenyl-3-methyl-4-cyclopentenone (yield, 42.6%; optical rotation, $[\alpha]_D^{20}$ −22.5° (C=1, chloroform); $n_D^{20}$ 1.4992) and 0.97 g of l-3-acetoxy-2-ω-butenyl-3-methyl-4-cyclopentenone (optical rotation, $[\alpha]_D^{20}$ −84.6° (C=1, chloroform); $n_D^{20}$ 1.4810).

The optical purity of d-4-hydroxy-2-ω-butenyl-3-methyl-2-cyclopentenone obtained by rearrangement of l-3-hydroxy-2-ω-butenyl-3-methyl-4-cyclopentenone according to Reference Example 1 was 98.1%.

EXAMPLE 14

Into the same flask as used in Example 1, dl-3-hydroxy-2-n-pentyl-3-methyl-4-cyclopentenone (18.2 g), triethylamine (0.1 g) and acetic anhydride (36 g) were charged, and the resultant mixture was stirred at 60°–80° C. for 3 hours. After completion of the reaction, the reaction mixture was subjected to the same work-up as in Example 11, followed by purification to give 21.9 g of dl-3-acetoxy-2-n-pentyl-3-methyl-4-cyclopentenone. Yield, 98%. B.P., 100°–110° C./0.1–0.3 mmHg.

The thus obtained dl-3-acetoxy-2-n-pentyl-3-methyl-4-cyclopentenone (2 g), Porcine Liver Esterase (manufactured by Sigma Inc.) (100 mg), 0.1M phosphate buffer (90 ml; pH 7) and methanol (10 ml) were mixed together, and the resultant mixture was vigorously stirred at 35° C. for 20 hours. After completion of the reaction, the reaction mixture was extracted with toluene (30 ml) two times. The same work-up as in Reference Example 1 gave 0.7 g of l-3-hydroxy-2-n-pentyl-3-methyl-4-cyclopentenone (yield, 43.1%; optical rotation, $[\alpha]_D^{20}$ −18.4° (C=1, chloroform); $n_D^{20}$ 1.4818) and 1.04 g of l-3-acetoxy-2-n-pentyl-3-methyl-4-cyclopentenone (optical rotation, $[\alpha]_D^{20}$ −69.4° (C=1, chloroform); $n_D^{20}$ 1.4708).

The optical purity of d-4-hydroxy-2-n-pentyl-3-methyl-2-cyclopentenone obtained by rearrangement of l-3-hydroxy-2-n-pentyl-3-methyl-4-cyclopentenone according to Reference Example 1 was 97%.

EXAMPLE 15

Into the same flask as used in Example 1, dl-3-hydroxy-2,3-dimethyl-4-cyclopentenone (12.6 g) and acetic anhydride (30 g) were charged, and the resultant mixture was stirred at 80°–100° C. for 3 hours. After completion of the reaction, the reaction mixture was subjected to the same work-up as in Example 11, followed by purification to give 16.2 g of dl-3-acetoxy-2,3-dimethyl-cyclopentenone. Yield, 96.5%. B.P., 52°–55° C./0.4–0.5 mmHg.

The thus obtained dl-3-acetoxy-2,3-dimethyl-4-cyclopentenone (2 g), Porcine Liver Esterase (manufactured by Sigma Inc.) (100 mg), 0.1M phosphate buffer (100 ml; pH 7) and methanol (10 ml) were mixed together, and the resultant mixture was vigorously stirred at 25°–30° C. for 24 hours. After completion of the reaction, the reaction mixture was extracted with methylisobutylketone (50 ml) three times. The solvent was removed from the extract, and the residue was purified by column chromatography using a mixture of ethyl acetate and toluene (3:5) as an eluent to give 0.46 g of l-3-hydroxy-2,3-dimethyl-4-cyclopentenone (yield, 31%; optical rotation, $[\alpha]_D^{20}$ −24.3° (C=1, chloroform); $n_D^{20}$ 1.4765) and 1.24 g of l-3-acetoxy-2,3-dimethyl-4-cyclopentenone (optical rotation, $[\alpha]_D^{20}$ −20.7° (C=1, chloroform); $n_D^{20}$ 1.4697).

The optical purity of d-4-hydroxy-2,3-dimethyl-2-cyclopentenone obtained by rearrangement of l-3-hydroxy-2,3-dimethyl-4-cyclopentenone according to Reference Example 1 was 90.2%.

EXAMPLE 16 dl-3-acetoxy-2-allyl-3-methyl-4-cyclopentenone (1 g) obtained in Example 11, esterase (manufactured by Sigma Inc., from wheat germ) (0.2 g) and 0.1M phosphate buffer (10 ml; pH 7) were mixed together, and the resultant mixture was stirred at 25°–30° C. for 35 hours. After completion of the reaction, the reaction mixture was extracted with methylisobutylketone (10 ml) three times. The solvent was removed from the extract and the residue was purified by column chromatography using a mixture of ethyl acetate and toluene (3:5) as an eluent to give 0.18 g of l-2-allyl-3-hydroxy-3-methyl-4-cyclopentenone. Optical purity, 80.2%.

EXAMPLES 17 TO 21

In the same manner as in Example 16 but using the hydrolase as shown in Table 2, the reaction was carried out as in Example 16. The results are shown in Table 2.

TABLE 2

| Example No. | Hydrolase (g) | Reaction condition Temperature (°C.) | Time (hr) | l-2-Allyl-3-hydroxy-3-methyl-4-cyclopentenone (I) Yield (g) | Optical purity (%) |
|---|---|---|---|---|---|
| 17 | Cholesterol esterase*[1] (0.2 g) | 25–30 | 30 | 0.21 | 92.4 |
| 18 | Esterase*[2] (1 g) | 25–30 | 30 | 0.2 | 81.2 |
| 19 | Stéapsin*[3] (1 g) | 25–30 | 40 | 0.06 | 75.8 |
| 20 | β-Amylase*[4] (0.2 g) (Type II-B) | 25–30 | 40 | 0.17 | 80 |
| 21 | Phosphatase*[5] (0.2 g) | 25–30 | 40 | 0.05 | 74.2 |

TABLE 2-continued

| Example No. | Hydrolase (g) | Reaction condition Temperature (°C.) | Time (hr) | l-2-Allyl-3-hydroxy-3-methyl-4-cyclopentenone (I) Yield (g) | Optical purity (%) |
|---|---|---|---|---|---|
| | (No. 3752) | | | | |

Note:
*[1]Produced from *Schizophyllum commune*; Toyo Boseki K. K.
*[2]Produced from *Candida cylindracea*; Sigma Inc.
*[3]Wako Pure Chemical Industries, Ltd.
*[4]Sigma Inc.
*[5]Sigma Inc.

EXAMPLE 22

Into a 500 ml Sakaguchi's flask, a liquid nutrient medium (composition: glucose, 1%; yeast extract, 0.3%; malt extract, 0.3%; polypeptone, 0.5%; pH, 5.6) (200 ml) was charged. After sterilization, *Candida krusei* OUT-6007 was inoculated therein and cultured at 30° C. for 2 days under shaking. dl-3-Acetoxy-2-allyl-3-methyl-4-cyclopentenone (4 g) was added thereto, and fermentation under shaking was continued at 30° C. for 24 hours for hydrolysis. After completion of the reaction, the resultant mixture was subjected to centrifugation, and the supernatant was extracted with methylisobutylketone (70 ml) four times. The solvent was removed from the extract, and the residue was purified by column chromatography using a mixture of ethyl acetate and toluene (3:5) as an eluent to give 1.5 g of l-2-allyl-3-hydroxy-3-methyl-4-cyclopentenone (yield, 48%; optical rotation, $[\alpha]_D^{20}$ −21.7° (C=1, chloroform)) and 1.96 g of l-3-acetoxy-2-allyl-3-methyl-4-cyclopentenone (optical rotation, $[\alpha]_D^{20}$ −82.6° (C=1, chloroform)).

The optical purity of l-2-allyl-3-hydroxy-3-methyl-4-cyclopentenone was 91%.

EXAMPLES 23 TO 32

In the same manner as in Example 22 but using the hydrolase as shown in Table 3 instead of *Candida krusei*, the reaction was carried out as in Example 22. The results are shown in Table 3.

TABLE 3

| Example No. | Type culture | l-3-Hydroxy-2-allyl-3-methyl-4-cyclopentenone Yield (g) | Optical purity (%) | Culture medium |
|---|---|---|---|---|
| 23 | *Hansenula anomala* var. *ciferrii* OUT-6095 | 1.63 | 90.2 | |
| 24 | *Metschnikowia pulcherrima* IFO-0561 | 1.25 | 85.6 | |
| 25 | *Pleurotus ostreatus* IFO-7051 | 0.96 | 92.3 | |
| 26 | *Bacillus subtilis* ATCC-6633 | 0.32 | 67.2 | Glucose 1%; yeast extract 0.5%; peptone 0.1%; $K_2HPO_4$ 0.05%; pH 7.0 |
| 27 | *Achromobacter parvulus* IFO-13181 | 0.3 | 21.3 | Glucose 1%; yeast extract 0.5%; peptone 0.1%; $K_2HPO_4$ 0.05%; pH 7.0 |
| 28 | *Flavobacterium lutesens* IFO-3084 | 0.25 | 12.3 | Glucose 1%; yeast extract 0.5%; peptone 0.1%; $K_2HPO_4$ 0.05%; pH 7.0 |
| 29 | *Chromobacterium iodinum* IFO-3558 | 0.15 | 8.6 | Glucose 1%; yeast extract 0.5%; peptone 0.1%; $K_2HPO_4$ 0.05%; pH 7.0 |
| 30 | *Nocardia uniformis* subptsuyamarenus ATCC-21806 | 1.26 | 46.2 | |
| 31 | *Torulopsis ernobii* IFO-0654 | 0.26 | 72.5 | |
| 32 | *Trichoderma longibrachiatura* IFO-4847 | 0.12 | 64.2 | |

EXAMPLES 33 TO 36

In the same manner as in Example 22 but using the starting material as shown in Table 4 instead of dl-3-acetoxy-2-allyl-3-methyl-4-cyclopentenone, the reaction was carried out as in Example 22. The results are shown in Table 4.

TABLE 4

| Example No. | Type culture | Starting material (g) | Product Name | Yield (g) | Optical purity (%) |
|---|---|---|---|---|---|
| 33 | *Hansenula anomala* var. *ciferrii* OUT-6095 | dl-3-Acetoxy-2-propargyl-3-methyl-4-cyclopentenone (3 g) | l-3-Hydroxy-2-propargyl-3-methyl-4-cyclopentenone | 0.85 | 90.1 |
| 34 | *Hansenula anomala* var. *ciferrii* OUT-6095 | dl-3-Acetoxy-2-n-pentyl-3-methyl-4-cyclopentenone (3 g) | l-3-Hydroxy-2-n-pentyl-3-methyl-4-cyclopentenone | 1.12 | 88.1 |
| 35 | *Candida krusei* | dl-3-Acetoxy-2- | l-3-Hydroxy-2- | 0.75 | 84.6 |

TABLE 4-continued

| Example No. | Type culture | Starting material (g) | Product Name | Yield (g) | Optical purity (%) |
|---|---|---|---|---|---|
| | OUT-6007 | propargyl-3-methyl-4-cyclopentenone (3 g) | propargyl-3-methyl-4-cyclopentenone | | |
| 36 | Candida krusei OUT-6007 | dl-3-Acetoxy-2-n-pentyl-3-methyl-4-cyclopentenone (3 g) | l-3-Hydroxy-2-n-pentyl-3-methyl-4-cyclopentenone | 1.21 | 86.2 |

EXAMPLE 37

Into a 500 ml Sakaguchi's flask, a nutrient medium (composition: glucose, 1%; yeast extract, 0.5%; peptone, 0.1%; $K_2HPO_4$, 0.05%; pH, 5.6) (200 ml) was charged. After sterilization, *Pseudomonas fragi* IFO-3458 was inoculated therein and cultured at 30° C. for 2 days under shaking. dl-3-Acetoxy-2-allyl-3-methyl-4-cyclopentenone (1.5 g) was added thereto, and fermentation under shaking was continued at 30° C. for 24 hours for hydrolysis. After completion of the reaction, the reaction mixture was subjected to centrifugation, and the supernatant was extracted with methylisobutylketone (50 ml) four times. The solvent was removed from the extract, and the residue was purified by column chromatography using a mixture of ethyl acetate and toluene (3:5) as an eluent to give 0.28 g of d-2-allyl-3-hydroxy-3-methyl-4-cyclopentenone (yield, 24%; optical rotation, $[\alpha]_D^{20}$ +22.5° (C=1, chloroform)) and 0.75 g of d-3-acetoxy-2-allyl-3-methyl-4-cyclopentenone (optical rotation, $[\alpha]_D^{20}$ +80.7° (C=1, chloroform); $n_D^{20}$ 1.4801).

d-2-Allyl-3-hydroxy-3-methyl-4-cyclopentenone was heated in trimethylamine to give R(−)-allethrolone, of which the optical purity was 94%.

EXAMPLE 38

To the same medium as in Example 37, dl-3-acetoxy-2-n-pentyl-3-methyl-4-cyclopentenone (2 g) was added, and fermentation under shaking was carried out at 30° C. for 30 hours for hydrolysis. After completion of the reaction, the reaction mixture was subjected to centrifugation, and the supernatant was extracted with methylisobutylketone (40 ml) two times. The same work-up and purification as in Example 37 gave 0.48 g of d-3-hydroxy-2-n-pentyl-3-methyl-4-cyclopentenone (yield, 30%; optical rotation, $[\alpha]_D^{20}$ +17.5° (C=1, chloroform); $n_D^{20}$ 1.4811) and 0.86 g of d-3-acetoxy-2-n-pentyl-3-methyl-4-cyclopentenone (optical rotation, $[\alpha]_D^{20}$ +60.8° (C=1, chloroform); $n_D^{20}$ 1.4703).

The optical purity of l-4-hydroxy-2-n-pentyl-3-methyl-2-cyclopentenone obtained by rearrangement of d-3-hydroxy-2-n-pentyl-3-methyl-4-cyclopentenone was 91%.

EXAMPLE 39

In the same manner as in Example 37 but using dl-3-acetoxy-2-propargyl-3-methyl-4-cyclopentenone (1.5 g) instead of dl-3-acetoxy-2-allyl-3-methyl-4-cyclopentenone, the hydrolysis was carried out as in Example 37, whereby 0.19 g of d-3-hydroxy-2-propargyl-3-methyl-4-cyclopentenone (yield, 16%; optical rotation, $[\alpha]_D^{20}$ +124° (C=1, chloroform); $n_D^{20}$ 1.5103) and 0.82 g of d-3-acetoxy-2-propargyl-3-methyl-4-cyclopentenone (optical rotation, $[\alpha]_D^{20}$ +14.6° (C=1, chloroform); $n_D^{20}$ 1.4943) were obtained.

The optical purity of l-4-hydroxy-2-propargyl-3-methyl-2-cyclopentenone obtained by rearrangement of d-3-hydroxy-2-propargyl-3-methyl-4-cyclopentenone was 93%.

EXAMPLE 40

In the same manner as in Example 37 but using dl-3-acetoxy-2-ω-butenyl-3-methyl-4-cyclopentenone (2 g) instead of dl-3-acetoxy-2-allyl-3-methyl-4-cyclopentenone, the hydrolysis was effected at 30° C. for 20 hours, and the supernatant was extracted with methylisobutylketone (40 ml) two times. The same work-up and purification as in Example 37 gave 0.32 g of d-3-hydroxy-2-ω-butenyl-3-methyl-4-cyclopentenone (yield, 20%; optical rotation, $[\alpha]_D^{20}$ +21.1° (C=1, chloroform); $n_D^{20}$ 1.4983) and 1.02 g of d-3-acetoxy-2-ω-butenyl-3-methyl-4-cyclopentenone (optical rotation, $[\alpha]_D^{20}$ +62° (C=1, chloroform); $n_D^{20}$ 1.4806) were obtained.

The optical purity of l-4-hydroxy-2-ω-butenyl-3-methyl-2-cyclopentenone obtained by rearrangement of d-3-hydroxy-2-ω-butenyl-3-methyl-4-cyclopentenone was 92%.

EXAMPLES 41 TO 43

In the same manner as in Example 37 but using the hydrolase as shown in Table 3 instead of *Pseudomonas fragi* IFO-3458, the reaction was carried out as in Example 37. The results are shown in Table 5.

TABLE 5

| Example No. | Type culture | l-3-Hydroxy-2-allyl-3-methyl-4-cyclopentenone | |
|---|---|---|---|
| | | Yield (g) | Optical purity (%) |
| 41 | Pseudomonas fluoresens IFO-3903 | 0.13 | 90.2 |
| 42 | Pseudomonas aeruginosa IFO-3080 | 0.11 | 88.6 |
| 43 | Pseudomonas testosteroni ATCC-11996 | 0.09 | 64.1 |

EXAMPLE 44

In the same manner as in Example 37 but using dl-2-allyl-3-octanoyloxy-3-methyl-4-cyclopentenone (2 g) instead of dl-3-acetoxy-2-allyl-3-methyl-4-cyclopentenone, the hydrolysis was effected. The same work-up as in Example 37 gave 0.3 g of d-2-allyl-3-hydroxy-3-methyl-4-cyclopentenone. Optical purity, 76%.

EXAMPLES 45 TO 54

A culture medium (10 ml) was charged into a test tube and, after sterilization, the microorganisms as shown in Table 6 were inoculated therein and fermentation under shaking was effected at 30° C. for 20 days. dl-3-Acetoxy-2-allyl-3-methyl-4-cyclopentenone (70 mg) was added to the medium, and cultivation was continued at 30° C. for 24 hours for hydrolysis. The rate of hydrolysis was as shown in Table 6.

TABLE 6

| Example No. | Type culture | Rate of hydrolysis (%) | Culture medium* |
|---|---|---|---|
| 45 | Rhodotorula rubra IFO-0870 | 4.7 | Y |
| 46 | Trichoderna longibrachiatum IFO-4847 | 5.3 | Y |
| 47 | Rhizopus chinensis IFO-4768 | 2.3 | Y |
| 48 | Mucor pusillus IFO-9856 | 8.2 | Y |
| 49 | Aspergillus niger ATCC-9642 | 3.5 | Y |
| 50 | Geotrichun candidum IFO-4597 | 2.8 | Y |
| 51 | Proteus vulgaris IFO-3851 | 6.3 | B |
| 52 | Citrobacter freundii IFO-12681 | 7.4 | B |
| 53 | Micrococcus lutens IFO-3066 | 4.6 | B |
| 54 | Gliocladium roseum IFO-5422 | 12.3 | Y |

Note:
*Y: glucose 1%, yeast extract 0.3%, malt extract 0.3%, peptone 0.5%, pH 5.6;
B: glucose 1%, yeast extract 0.5%, peptone 0.1%, $K_2HPO_4$ 0.05%, pH 7.0.

What is claimed is:

1. A process for producing 4-cyclopentenones of the formula:

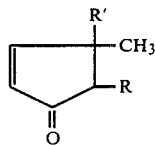

wherein R is a lower alkyl group, a lower alkenyl group or a lower alkynyl group and R' is a hydroxyl group or an aliphatic acyloxy group, provided that the substituent R at the 2-position and the methyl group at the 3-position take a cis-configuration in the d- or l-form, which comprises hydrolyzing the corresponding 4-cyclopentenone wherein R' is an aliphatic acyloxy group in the dl-form with a microorganism or enzyme having a capability of selective hydrolysis of the d- or l-form in said starting corresponding 4-cyclopentenone in the dl-form to selectively obtain either the d- or l-form 4-cyclopentenone product.

2. The process according to claim 1, wherein the starting 4-cyclopentenone wherein R' is an aliphatic acyloxy group in the dl-form is prepared by reacting the corresponding 3-hydroxy-4-cyclopentenone of the formula:

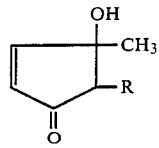

wherein R is a lower alkyl group, a lower alkenyl group or a lower alkynyl group, provided that the substituent R at the 2-position and the methyl group at the 3-position take a cis-configuration with an aliphatic carboxylic acid halide as anhydride.

3. The process according to claim 1, wherein the microorganism or enzyme is selected from the microorganisms belonging to any one of Rhodotorula, Trichloderma, Candida, Pseudomonas, Hansenula, Bacillus, Achromobacter, Nocardia, Chromobacterium, Flavobacterium, Rhizopus, Mucor, Aspergillus, Alcaligenes, Torulopsis, Corynebacterium, Endomyces, Saccharomyces, Arthrobacter, Metshnikowia, Pleuortus, Streptomyces, Proteus, Gliocladium, Acetobacter, Helminthosporium, Brevibacterium, Escherichia, Citrobacter, Micrococcus, Pediococcus, Klebsiella, Absidia and Geotrichem, or the enzymes produced by the said microorganisms.

4. The process according to claim 1, wherein the microorganism or enzyme is selected from the microorganisms belonging to Pseudomonas, or the enzymes produced from the said microorganisms, and the product is a d-4-cyclopentenone.

5. The process according to claim 4, wherein the microorganism or enzyme is selected from the microorganisms belonging to Pseudomonas fragi, Pseudomonas fluorescens and Pseudomonas aeruginosa, or the enzymes produced by the said microorganisms.

6. The process according to claim 1, wherein the microorganism or enzyme is selected from the microorganisms belonging to Trichoderma, Candida, Hansenula, Bacillus, Achromobacter, Nocardia, Chromobacter, Flavobacterium, Torulopsis, Metshnikowia and Pleurotus, or the enzymes produced from the said microorganisms or any plant or animal, and the product is an l-4-cyclopentenone.

7. The process according to claim 6, wherein the microorganism or enzyme is selected from the microorganisms belonging to Candida cylindracea, Hansenula anomala var. ciferrii, Metshnikowia pulcherrima, Pleurotus octreatus, Schizophyllum commune, Candida krusei, Bacillus subtilis, Achromobacter parvulus, Flavobacterium lutesens, Chromobacterium iodinum, Nocardia uniformis subptsuyamanenus, Torulopsis ernobii and Trichoderma longibrachiatum, or the enzymes produced from the said microorganisms or pig liver, horse liver or wheat.

8. The process according to claim 1, wherein said enzyme is a member selected from the group consisting of pig liver esterase, pig pancreas esterase, horse liver esterase, dog liver esterase, pig phosphatase, β-amylase obtainable from barley and potatoe and lipase obtainable from wheat.

9. The process according to claim 1 for the hydrolysis of a d-2-substituted-3-acyloxy-3-methyl-4-cyclopenentone to a l-2-substituted-3-hydroxy-3-methyl-4-cyclopentenone, wherein said microorganism or enzyme is a member selected from the group consisting of pig liver esterase, horse liver esterase, Candida cylindracea, Hansenula anomala var. ciferrii, Metshnikowia pulcherrima, Pleurotus ostreatus, cholesterol esterase and Candida krusei.

10. The process according to claim 1 for the hydrolysis of a 1-2-substituted-3-acyloxy-3-methyl-4-cyclopentenone to a d-2-substituted-3-hydroxy-3-methyl-4-cyclopentenone, wherein said microorganism or enzyme is a member selected from the group consisting of Pseudomonas fragi, Pseudomonas fluorescens, Pseudomonas alruginosa and enzymes produced thereby.

11. The process according to claim 1, wherein said microorganism or enzyme is Pseudomonas or an enzyme produced thereby for the hydrolysis of a 1-2-substituted-3-acyloxy-3-methyl-4-cyclopentenone to a d-2-substituted-3-hydroxy-3-methyl-4-cyclopentenone.

* * * * *